United States Patent
Navarro

(10) Patent No.: US 6,682,506 B1
(45) Date of Patent: Jan. 27, 2004

(54) DEVICE FOR MAINTAINING AT LEAST A TUBE

(76) Inventor: Francis Navarro, 4, rue des Chapeliers, Nimes (FR), 30000

( * ) Notice: Subject to any disclaimer, the term of this patent is extended or adjusted under 35 U.S.C. 154(b) by 0 days.

(21) Appl. No.: 09/868,999

(22) PCT Filed: Dec. 22, 1999

(86) PCT No.: PCT/FR99/03258

§ 371 (c)(1),
(2), (4) Date: Sep. 21, 2001

(87) PCT Pub. No.: WO00/37136

PCT Pub. Date: Jun. 29, 2000

(30) Foreign Application Priority Data

Dec. 22, 1998 (FR) .............................. 98 16247

(51) Int. Cl.[7] .................................. A61M 5/32
(52) U.S. Cl. ..................... 604/174; 604/541; 604/539
(58) Field of Search ................. 604/174–175, 604/93.01, 180, 540–541, 543, 539; 128/DIG. 26

(56) References Cited

U.S. PATENT DOCUMENTS 3,896,810 A * 7/1975 Akiyama ................... 604/117
5,167,639 A * 12/1992 Hollands et al. ............ 604/180
5,364,367 A * 11/1994 Banks et al. ................. 604/174
5,569,207 A   10/1996 Gisselberg et al.
5,735,833 A *  4/1998 Olson .......................... 604/23
5,807,341 A *  9/1998 Heim .......................... 604/174
6,355,020 B1 * 3/2002 Bousquet .................... 604/175

FOREIGN PATENT DOCUMENTS

| EP | 0 082 596 | 6/1983 |
| GB | 0 082 596 | * 11/1982 |
| GB | 2128481 | 5/1984 |
| WO | WO91/07204 | 5/1991 |
| WO | WO97/45148 | 12/1997 |

* cited by examiner

Primary Examiner—LoAn H. Thanh
(74) Attorney, Agent, or Firm—Leydig, Voit & Mayer, Ltd.

(57) ABSTRACT

A device for retaining at least one drainage tube passing through an artificial cavity into a patient's body. According to the invention, the device includes at least one collecting chamber for the collection of secretions, a base attached to the body and surrounding each collecting chamber, and at least one orifice in the collecting chamber for the passage of a drainage tube, the axis of the orifice not being perpendicular to the plane of the base, enabling the drainage tube to be curved.

5 Claims, 3 Drawing Sheets

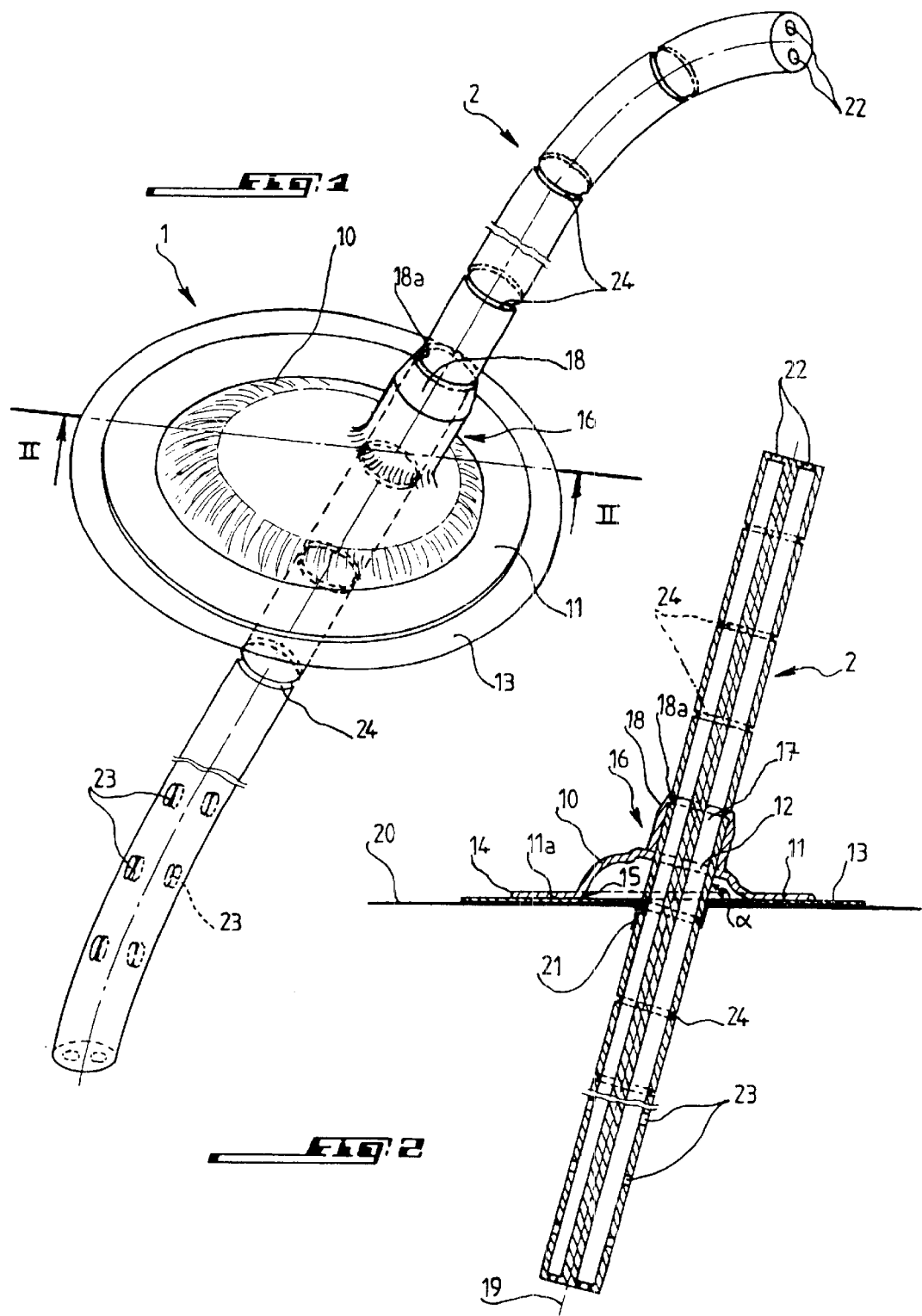

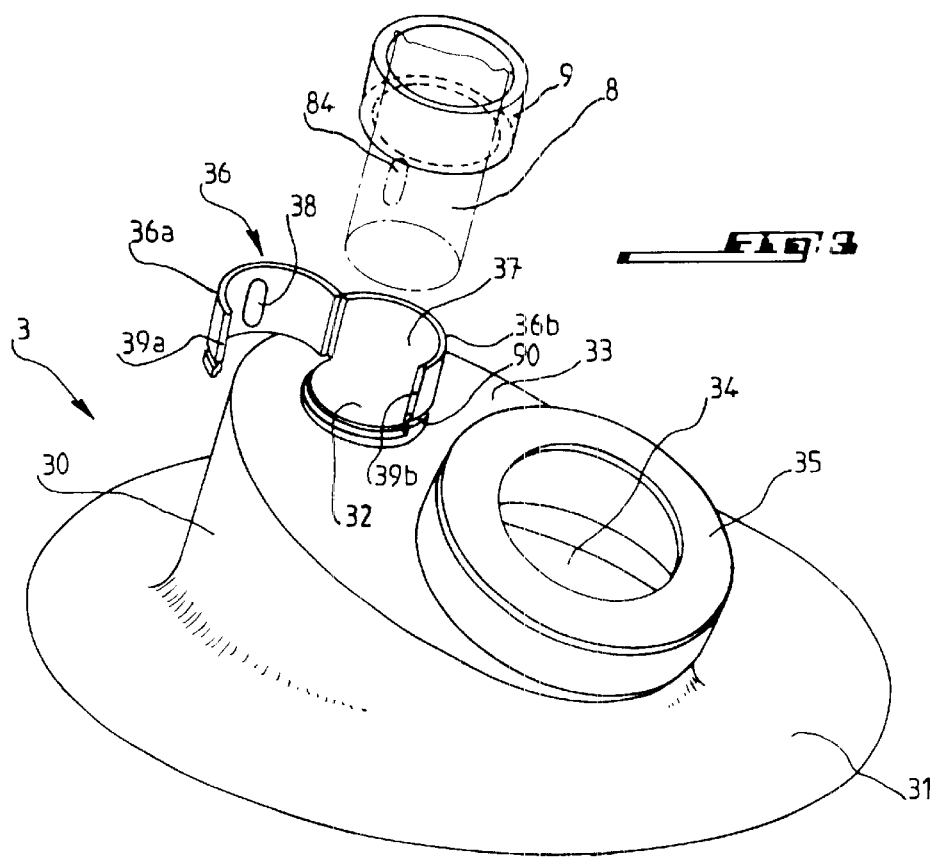
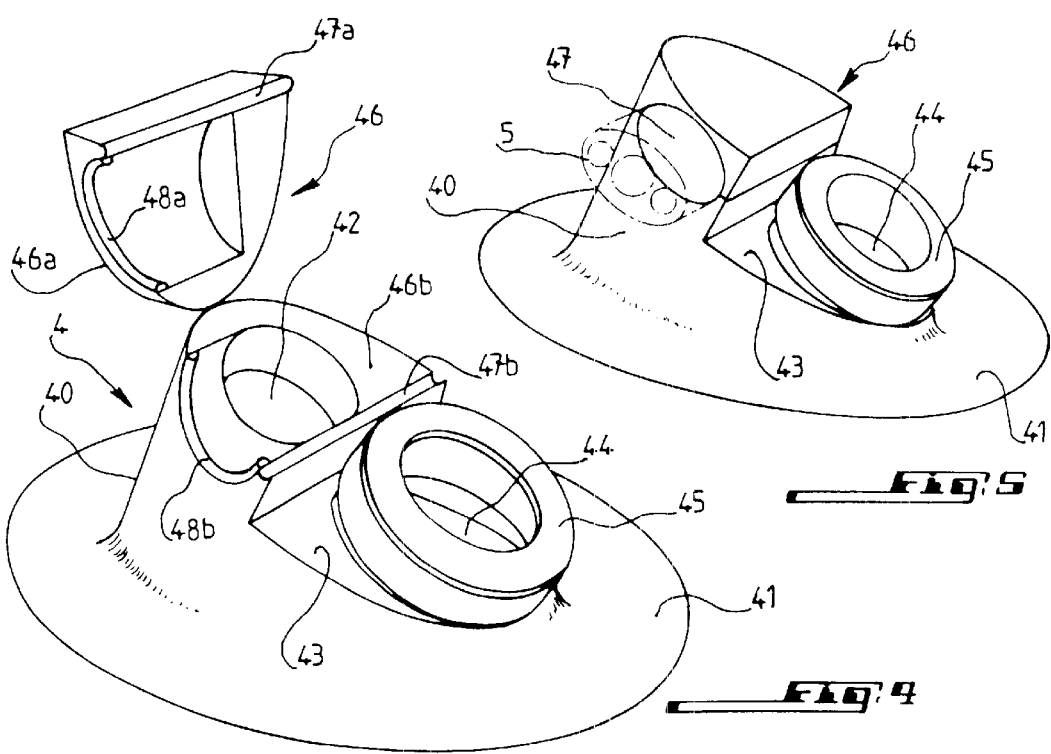

DEVICE FOR MAINTAINING AT LEAST A TUBE

FIELD OF THE INVENTION

The invention concerns a device for retaining at least one drainage tube or the like, passing through an artificial orifice in a patient's body.

BACKGROUND

It is often necessary in surgery and intensive care to carry out thoracic or abdominal drainage. Drainage consists of putting the interior of the thorax or the abdomen in communication with an aspiration system, generally to empty discharge from the pleural or abdominal cavity, or to drain an operating site or a hollow organ like the stomach, the intestine, the bile ducts, or the esophagus.

The attachment of the drainage tube is usually ensured by a suture to the skin, with dressing provided around the drainage tube.

This poses numerous problems.

Attachment by suturing is painful for the patient because of the pull exerted on the drainage tube, and it is a source of infection.

Because of its connection to the aspiration system, the drainage tube has a tendency to bend near the orifice made in the patient's body. This is also a source of pain for the patient. Furthermore, the presence of dressings makes for difficult access to the drainage tube in order to verify its position or even the presence of possible secretions, Finally, several days after surgery, the drainage tube must be progressively withdrawn in two or three steps from the patient's body.

Each time, it is necessary to cut the thread, possibly to attach it to the skin with a new suture. It is also necessary to redo all the dressings, and especially to put in place a new pocket for collection of the secretions.

These manipulations are painful for the patient, and constitute a risk of infection at the cutaneous orifice and significant work for the nursing staff. They are expensive as much for the labor as for products used.

That is why different systems have been emphasized to hold such drainage tubes in position.

It can especially be noted that document FR-2 707 175 describes a device realized as two separable, approximately semicylindrical elements, and that is attached to the patient's body by an adhesive zone. Furthermore, the dressing can be replaced by a piece of absorbent material placed between the device and the adhesive zone. Near the patient's body, the drainage tube extends approximately perpendicular to the body.

This device makes it possible to effectively ensure that the drainage tube is held in place on the patient's body, without the necessity of a suture to the skin.

However, such a device does not make it possible to give a particular orientation to the drainage tube that is inclined toward the patient's body. It no longer enables sampling of possible secretions which appear at the orifice in the patient's body.

SUMMARY OF THE INVENTION

The same applies for the rigid connector described in document WO 97/45148.

The invention has the goal of mitigating these drawbacks by proposing a device for retaining at least one drainage tube or the like, such as a probe, a plate, or a microtubular drainage tube, allowing curvature and orientation of the drainage tube at its exit from the orifice in the patient's body without generating strain and therefore pain for the patient, and without causing risk of displacement of the drainage tube.

Thus, the invention concerns a device for retaining at least one drainage tube or the like passing through an artificial cavity in a patient's body, characterized in that it comprises at least one collecting chamber for collection of possible secretions, a base designed to be attached to said body and surrounding each collecting chamber, as well as at least one orifice in the collecting chamber for passage of a drainage tube or the like, the axis of said orifice not being perpendicular to the plane of the base, enabling the drainage tube to be curved and thus to orient it with respect to the patient's body.

Preferably, the orifice for the drainage tube is extended by a support including a cavity for the drainage tube.

In a first embodiment method, the cavity of the support is oriented such that its axis corresponds approximately to that of the orifice.

In a second embodiment method, the cavity of the support is oriented such that its axis is inclined relative to that of the orifice.

Preferably, the support for the drainage tube is constituted of two hinged parts.

The support for the drainage tube advantageously includes means working together with the drainage tube to secure it in position relative to the device.

In an embodiment variant, these securing means are formed of a skirt in the extension of the support, this skirt converging towards the axis of the cavity of the support and intended to be snapped in a transverse groove provided on said drainage tube, especially by means of a ridge which preferably terminates it.

In another embodiment variant, these securing means are formed of at least one protuberance provided on the wall of the cavity of the support and intended to be snapped in a longitudinal or transverse groove provided on the drainage tube.

The base of the device according to the invention advantageously includes an adhesive layer on the surface intended to make contact with a patient's body.

In one embodiment method, this adhesive layer can be extended towards the exterior of the base.

In another embodiment method, this adhesive layer extends beyond the interior part of the base to partially close off the collecting chamber.

Preferably, the adhesive layer is made from an adhesive gum capable of absorbing secretions.

Preferably, a collecting chamber of the device according to the invention also includes an orifice for a pocket for collection of secretions.

Preferably, a collecting chamber of the device according to the invention includes at least one window, especially for taking samples.

Moreover, the device according to the invention is preferably oriented on the patient's body to favor drainage by gravity.

When the device includes an orifice for a pocket for collection of secretions, they are then easily drained toward the pocket.

BRIEF DESCRIPTION OF THE DRAWINGS

The invention will be better understood and its other goals, advantages and characteristics will appear more clearly by reading the description that follows of nonlimiting embodiment examples of the invention, this description being made with regard to the appended drawings, in which:

FIG. 1 is an oblique view of a first example of the retaining device according to the invention, with one drainage tube;

FIG. 2 is a transverse section along II—II in FIG. 1;

FIG. 3 is an oblique view of a second embodiment example of the retaining device according to the invention, with one drainage tube;

FIG. 4 is an oblique view of a third embodiment example of a retaining device according to the invention, in the unused state;

FIG. 5 is an oblique view of the retaining device illustrated in FIG. 4, used with one drainage tube;

DETAILED DESCRIPTION

Figure 6:
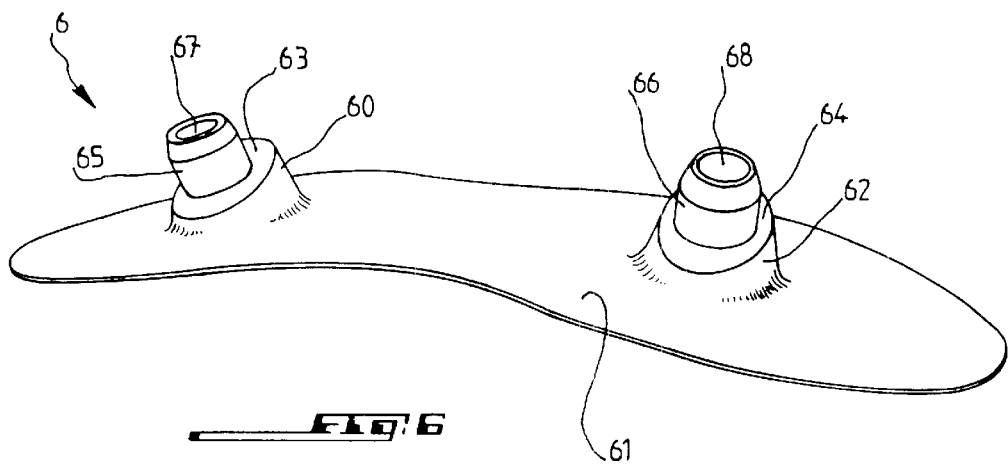
FIG. 6 is an oblique view of a fourth embodiment example of the retaining device according to the invention.

First, refer to FIGS. 1 and 2 which show a retaining device 1 according to the invention, comprising a collecting chamber 10, a base 11 surrounding the collecting Chic chamber 10, and an orifice 12 for passage of a drainage tube 2.

The base 11 is designed to be attached to a patient's body, especially by means of an adhesive layer 13 attached to the base on its surface 11a opposite the collecting chamber 10.

This adhesive layer 13 can be placed on all or part of the surface 11a of the base 11. It can also, as illustrated in FIGS. 1 and 2, extend beyond the exterior periphery 14 of the base 11 and also extend beyond the interior part 15 of the base, to partially close the collecting chamber 10.

As shown more precisely in FIG. 2, in this case the adhesive layer simply makes a passage for the drainage tube 2.

Preferably, this adhesive layer 13 is made from adhesive gum capable of absorbing secretions, for example a natural gum of the pectin or gelatin type, or a gum described in the document EP-92999, the contents of which are included for reference in the present application.

In practice, this adhesive layer 13 is protected by an appropriate film (not illustrated) that is removed before any use of device 1.

In the embodiment example illustrated with FIGS. 1 and 2, chamber 10 has a convex or dome-shaped form. The orifice 12 for the drainage tube 2 is made in the wall of the collecting chamber 10 such that the axis 19 of the orifice 12 is not perpendicular to the plane of the base 11.

In practice, the orifice 12 is therefore not made in the central part of the dome of the collecting chamber 10, but is displaced.

The use of the retaining device I according to the invention is the following.

A drainage tube 2 is first placed in a patient's body by passing through cavity 21 made in the body.

In the example illustrated in the figures, drainage tube 2 includes channels 22.

In its lower part, designed to be placed in the body, drainage tube 2 includes perforations 23 for the collection of secretions.

In its upper part, designed to be placed outside the patient's body, drainage tube 2 includes continuous transverse grooves 24, the function of which will be explained later.

Once the drainage tube is in position in the patient's body, device 1 is made to slide along the upper part of the drainage tube 2 until the base 11 is supported on the body 20 of the patient.

Device 1 is then attached to the patient's body by means of the adhesive layer 13.

The device is preferably attached such that the left part of FIG. 3 corresponds to the upper part of the patient's body, and the right part to the lower part.

As indicated previously, the axis of the orifice 12 is not perpendicular to the plane of the base 11. For that reason, by passing through the orifice 12, drainage tube 2 is no longer perpendicular to the base 11.

Preferably, the less than 90° angle $\alpha$ made by the axis 19 of the orifice 12 relative to the plane of the base 11 is between 5° and 85°, and advantageously between 45° and 60°.

As a result of this particular inclination of the axis of the orifice 12, drainage tube 2 can be inclined, and in particular tilted back towards body 20 of the patient, without strain being generated at the level of cavity 21.

The curvature given to the drainage tube is thus not painful for the patient, and it does not cause any displacement of the drainage tube. This curvature is allowed because of the presence of the collecting chamber.

The retaining device illustrated in FIGS. 1 and 2 also includes a support 16 that extends the orifice 12 towards the exterior of the collecting chamber 10.

This support includes a cavity 17 enabling passage of the drainage tube.

In this embodiment example, support 16 is arranged such that the axis of the cavity 17 corresponds approximately to that of the orifice 12.

At its free end, the support 16 includes a skirt 18 which converges slightly towards the axis of the cavity 17 and therefore towards the drainage tube when the device 1 is placed on it.

Preferably, this skirt ends with a ridge 18a that is designed to cooperate with transverse grooves 24 of the drainage tube to better attach the drainage tube 2 relative to device 1 and to seal the assembly.

When progressive withdrawal of the drainage tube 2 from the patient's body is carried out, the skirt 18 snaps onto different grooves.

During drainage, secretions can accumulate around orifice 12. This can involve liquids arising from the interior of the patient's body, or even bleeding produced around cavity 21.

These secretions are thus collected inside the collecting chamber 10.

Moreover, they can originate from infections, and it is therefore useful to monitor the presence of such secretions, and also to undertake samplings to analyze them.

That is why a window (not illustrated in the drawings) is advantageously provided in the wall of the collecting chamber 10. In particular, this window can be closed by a membrane or a transparent plug.

If the device is attached to the body as indicated previously, the secretions accumulate in the bottom part of the collecting chamber (on the right in FIG. 3) and provision must preferably be made for the window at this level.

The retaining device 1 illustrated in FIGS. 1 and 2 can be used in thoracic or abdominal surgery.

The drainage tube is not necessarily round in cross section, but can also be oval in cross section.

Other embodiment examples of the retaining device according to the invention will be described with reference to FIGS. 3 to 7. The characteristics and advantages common to the example described with reference to FIGS. 1 and 2 will not be described again.

Reference is now made to FIG. 3, which illustrates a second embodiment example of the retaining device according to the invention This device 3 also includes a collecting chamber 30 and a base 31 surrounding it.

The collecting chamber has the general shape of a truncated cylinder.

It includes on its upper surface 33 an orifice 32 for a drainage tube 8 or the like.

The orifice 32 is extended by a support 36 including a cavity 37 for the drainage tube 8.

The support 36 is formed from two hinged parts 36a and 36b. It is represented in open position in FIG. 3.

This figure shows that the axis of the cavity 37, like that of the orifice 32, is not perpendicular to the base 31 as a result of the inclination of the upper surface 33 of the collecting chamber 30 relative to the plane of the base 31.

The support 36 includes at least one protuberance 38 on its interior surface. When a drainage tube 8 passes through the orifice 32 and the cavity 37, this protuberance 38 on the wall of the cavity 37 is snapped into a longitudinal groove 84 provided on drainage tube 8.

This protuberance 38 therefore makes it possible to better attach the drainage tube 8 in position relative to the device 3.

The hinged parts can be secured in closed position by a snapping means. In the example illustrated in FIG. 3, this means is formed from a semicylindrical part 39a provided on the free lateral edge of part 36a of the support and a groove 39b provided in the free lateral edge of the part 36b of the support and designed to receive the semicylindrical part 39a.

They can also be secured in closed position by means of collar 9. This then is snapped in groove 90 provided at the base of the support 36.

Moreover, the protuberance 38 can be omitted. In this case, as with support 16 illustrated in FIGS. 1 and 2, the support 36 is extended by a skirt slightly convergent towards the axis of the cavity 37. A ridge can also be provided on the free annular edge of this skirt. The skirt is then designed to be snapped into a transverse groove provided on the drainage tube. This embodiment method is not illustrated in FIG. 3.

In the example illustrated in FIG. 3, another orifice 34 is made in the upper wall 33 of the collecting chamber 30. This orifice is extended by a skirt 35 designed for attachment of a pocket for collection of secretions (not illustrated).

The device of the invention is preferably oriented on a patient's body so that the gravity in the bottom of the collecting chamber 30, which facilitates drainage and evacuation in the pocket for collection of secretions.

The retaining device 3 can in particular be used in abdominal or thoracic surgery for drainage tubes of intermediate size, between 5 and 7 mm.

Also, device 3 might not include orifice 34 for the attachment of a pocket for collection of secretions.

Device 3 provides advantages similar to those of device 1 illustrated in FIGS. 1 and 2.

Furthermore, the drainage tube or the like placed in the device 3 can be thinner than that of the drainage tube 2 used with device 1. In fact, it is sufficient for drainage tube 8 to have a section sufficiently thick to make groove 84, therefore the thickness of the drainage tube can be less. Drainage tube 8 is therefore less rigid than drainage tube 2 illustrated in FIGS. 1 and 2. It can be round or oval in cross section.

FIGS. 4 and 5 illustrate a third embodiment example of the retaining device according to the invention.

This device 4, like device 3, includes a collecting chamber 40 presenting the general shape of a truncated cylinder, with a base 41 surrounding the chamber 40.

The collecting chamber 40 therefore includes an upper surface 43 which is inclined relative to the plane of the base 41.

An orifice 42 for the drainage tube or the like and an orifice 44 for a pocket for collection of secretions are made in this upper surface 43.

As indicated previously for device 3, the orifice 44 and the skirt 45 for attachment of the pocket for secretions could be omitted.

The orifice 42 for a drainage tube or the like is extended by a support 46 that is formed from two units 46a and 46b hinged to each other.

The support 46, which has the shape of a case, is in open position in FIG. 4 and in closed position in FIG. 5.

The support 46 includes a cavity 47 for the passage of a drainage tube 5.

As FIGS. 4 and 5 show, the support 46 is arranged, relative to the orifice 42, such that the axis of the cavity 47 does not coincide with that of the orifice 42, but rather is inclined relative to it.

When the device 4 is put in place on a drainage tube 5 or the like, the support 46 is at first in open position. Drainage tube 5 then passes through the orifice 42, drainage tube 5 not being orthogonal to the plane of the base as a result of the inclination of the orifice 42.

After attachment of the device 3 to a patient's body, support 46 is closed by swinging part 46a onto part 46b.

The support 46 is kept in closed position, for example by snapping. The upper part 46a of the support can then include on its free longitudinal edge a semicylindrical part 47a, and the lower part 46b of the support, also on its free longitudinal edge, [can include] a groove 47b designed to receive the semicylindrical part 47a.

The support 46 thus makes it possible to give the drainage tube 5 an orientation that is different from that of the drainage tube when it is in orifice 42.

In practice, the support 46 thus makes it possible to place the drainage tube 5 in a position approximately parallel to the patient's body.

Means contributing to retaining the drainage tube in the case 46 can be provided on the wall of the cavity 47.

In the example illustrated in FIG. 4 these means comprise a ring or ridge constituted in two parts 48a and 48b and formed on the wall of the cavity 47.

This ring is designed to be snapped into a transverse groove (not illustrated) provided on the drainage tube 5 to contribute to the [sealing] tightness of the assembly.

The retaining device 4 can also be used in thoracic or abdominal surgery for drainage tubes with an intermediate size between 5 and 7 mm. The drainage tube can equally well have an oval or a round shape.

FIG. 6 illustrates a fourth example of the retaining device according to the invention.

This device 6 includes two collecting chambers 60 and 62 with a base 61 surrounding these two chambers.

In contrast to the device illustrated in FIGS. 1 to 5, the base 61 is not planar but has a slightly concave shape to match the shape of the patient's body, and in particular the shape of the rib cage.

Each chamber 60, 62 has the general shape of a truncated cylinder, the upper surface 63, 64 of which is inclined relative to the base 61.

Provided in each upper surface 63, 64 is an orifice, for a drainage tube or the like, which is extended by support 65, 66. Each support 65, 66 includes a cavity 67, 68 for a drainage tube. These supports 65 and 66 will not be described in more detail, reference being made to the preceding description.

Thus, the axis of the cavity 67 is not perpendicular to the plane of the base, or even to the plane passing through the zone joining the chamber 60 and the base 61. The same applies for cavity 68.

In the example illustrated in FIG. 6, the collecting chambers 60 and 62 are oriented differently relative to the base 61.

This retaining device 6 is therefore used in particular in thoracic surgery and for drainage tubes ranging from 3 to 10 mm in dimension. Such a device makes it possible to attach several drainage tubes to the same base.

It also presents the advantage of maintaining the relative position of the drainage tubes, of placing several drainage tubes in the same space with minimal overcrowding, and of providing reinforcement of retention on the patient's body.

Figure 7:
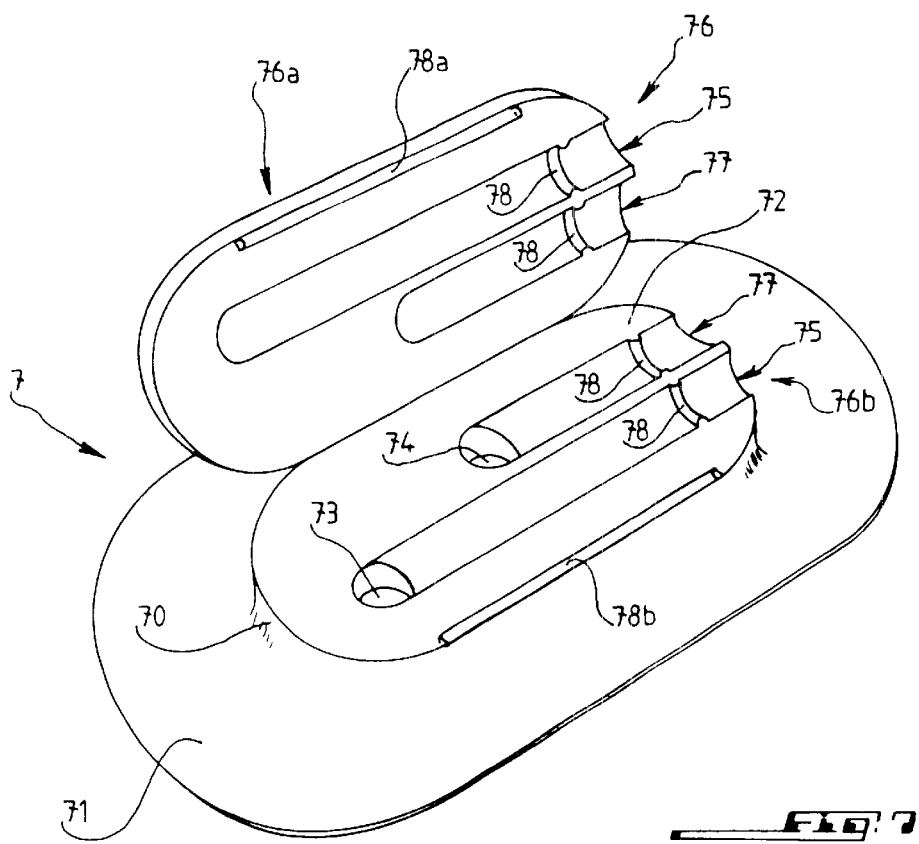
FIG. 7 is an oblique view of a fifth embodiment example of the retaining device according to the invention.

FIG. 7 illustrates a fifth embodiment example of the retaining device according o the invention.

This device 7 also includes a collecting chamber 70 and a base 71 that surrounds he chamber 70 and is designed to be attached to a patient's body.

The collecting chamber 70 presents an upper surface 72 which is approximately parallel to the base 71.

In this upper surface 72 are provided two orifices 73, 74, the axes of which are preferably not perpendicular to the plane of the base.

These orifices 73, 74 advantageously have an oval shape that provides clearance for passage of a drainage tube or the like, and that facilitates positioning the device 7 on a patient's body and curvature of the drainage tube.

These orifices 73, 74 are extended by a support 76 that is common to both orifices.

This support forms a case in which the lower part 76b is made in the upper wall 72 of the collecting chamber, whereas the upper part 76a forms a cover, hinged on the collecting chamber to close on it.

This support is held in the closed position, for example by snapping. The upper part 76a forming the cover can include in this case a semicylindrical part 78a on its free longitudinal edge, and a corresponding groove 78b on the lower part 76b that is designed to receive the semicylindrical part 78a.

The case 76 defines two cavities 75, 77 each extending orifice 73, 74.

In the example illustrated in FIG. 7, the support 76 is made so that drainage tubes or the like passing into the orifices 73, 74 and then into cavities 75, 77 are made approximately parallel to the base 71 and therefore to the patient's body.

That is why the device 7 is conceived for parts of the body that are intended to be supported, in particular on a bed, to avoid any pull. It could therefore be used, for example, in back surgery.

This device 7 is especially designed for drainage tubes that are small in size, between 3 and 5 mm.

Thus, the device 7 makes it possible to bend drainage tubes without exerting pull and while protecting them by means of case 76.

The case 76 could be designed to give other orientations to the drainage tubes.

This case in itself secures drainage tubes or the like in position relative to the device 7. This attachment can be reinforced by means of rings or bends 78 provided in the cavities 75 and 77 and which cooperate with the transverse grooves provided in the drainage tubes (not illustrated), their cooperation making the assembly tight.

Of course, the invention is not limited to the embodiments just described. In particular, a device according to the invention could include more than two collecting chambers on the same base, or more than two orifices for drainage tubes on the same connection chamber. In addition, any position whatsoever of the axis of the opening for a drainage tube or the like relative to the axis of the drainage tube support extending this orifice is possible, and can be chosen according to the desired application.

Furthermore, an opening for attachment of a pocket for collection of secretions can be provided on any retaining device according to the invention.

The preceding description has been made essentially for drainage tubes. However, the device according to the invention can also be used for holding probes, in particular nasogastric ones, or even for plates with an undulating structure or microtubular drainage tubes that enable the evacuation of fluids by capillarity.

Plugs are also envisioned the shape of which is adapted to that of the opening for the drainage tube or of the cavity of the drainage tube support. These plugs act to close the opening or cavity when the drainage tube is withdrawn from the patient's body. When the device according to the invention is used in thoracic surgery, these plugs have sufficient length to come into contact with the cavity in the patient's body and thus avoid any entrance of air.

Finally, the reference numbers inserted after the technical characteristics appearing in the claims have the goal only of facilitating their comprehension, and should not limit their scope.

What is claimed is:

1. A device for retaining at least one drainage tube passing through an artificial cavity in a patient's body, comprising
   a drainage tube, and
   at least one collecting chamber for collection of secretions, wherein
      the collecting chamber is defined by an upper wall closing the collecting chamber, the upper wall including a tubular support, the tubular support including two hinged parts, and a base for attachment to the patient's body and surrounding the collecting chamber, and a lateral wall connecting said base to said upper wall,
      said upper wall is inclined relative to said base and has at least one orifice for passage of the drainage tube through said collecting chamber so that the drainage tube can be inclined relative to the patient's body and said inclined upper wall, wherein the tubular support extends from the orifice and includes an opening for receiving the drainage tube,
      and said lateral wall, said upper wall, and said base are together slidable along a part of the drainage tube towards the patient's body once the drainage tube has been introduced into the cavity in the patient's body, until said base comes into contact with the patient's body, and
      the drainage tube may be withdrawn from the patient's body by sliding the drainage tube relative to said collecting chamber.

2. The device according to claim 1, wherein said support forms a case having an upper hinged part and a lower hinged part, wherein said lower hinged part is located in said upper wall of said collecting chamber and said upper part is hinged to said collecting chamber for closing said support.

3. The device according to claim 2, wherein the drainage tube is oriented in a position approximately parallel to the patient's body when said support is closed.

4. The device according to claim 1, including snapping means for securing said two hinged parts in a closed position.

5. The device according to claim 1, wherein said two hinged parts have semicylindrical configurations, said two hinged parts being hinged at a first lateral edge and securable at a second lateral edge.

* * * * *